United States Patent [19]

Jordan

[11] 4,050,737
[45] Sept. 27, 1977

[54] SUPPORT HARNESS

[76] Inventor: Ruth Frances Jordan, 3095 Monticello Blvd., Cleveland Hts., Ohio 44118

[21] Appl. No.: 718,832

[22] Filed: Aug. 30, 1976

[51] Int. Cl.² .......................................... A47D 13/08
[52] U.S. Cl. .................................... 297/389; 128/134
[58] Field of Search ............... 297/389, 219, 229, 275; 128/134

[56] References Cited

U.S. PATENT DOCUMENTS

| 3,099,486 | 7/1963 | Scott | 297/389 |
|---|---|---|---|
| 3,301,594 | 1/1967 | Pukish | 297/389 |
| 3,315,671 | 4/1967 | Creelman | 128/134 |
| 3,604,750 | 9/1971 | Doering | 297/389 |
| 3,791,694 | 2/1974 | Roberts | 297/389 |
| 3,889,668 | 6/1975 | Ochs et al. | 128/134 |

FOREIGN PATENT DOCUMENTS

| 728,849 | 4/1955 | United Kingdom | 297/389 |

Primary Examiner—Francis K. Zugel
Attorney, Agent, or Firm—Donnelly, Maky, Renner & Otto

[57] ABSTRACT

A support harness for a child who, due to brain damage or disease, lacks trunk or head control sufficient to achieve or maintain a normal sitting position, said support harness being characterized in that it comprises two layers of a fabric which combines firmness and softness and which is of shape to define a back portion with upper and lower strap means for fastening the harness to the backrest of a chair; laterally extending side flaps (with foam rubber or like padding therein) adapted to be wrapped over the sides of the child's body between the armpits and the hips and across the chest and abdomen and secured together in overlapping relation by releasable fastening means; a longitudinal flap from the lower end of the back portion which is of progressively narrowing width to pass through the child's crotch and upwardly over the overlapped lateral flaps; and shoulder straps for releasably interconnecting the upper ends of said longitudinal flap and back portion.

The support harness herein is further characterized in that it may be provided with a flat, rigid back portion for use with chairs having rounded backrests or for use in conjunction with adult-size chairs with a foam rubber pillow or pillows inserted between the backrest of the chair and the rigid back portion of the harness so that the child's legs will hang comfortably from the front edge of the chair.

8 Claims, 10 Drawing Figures

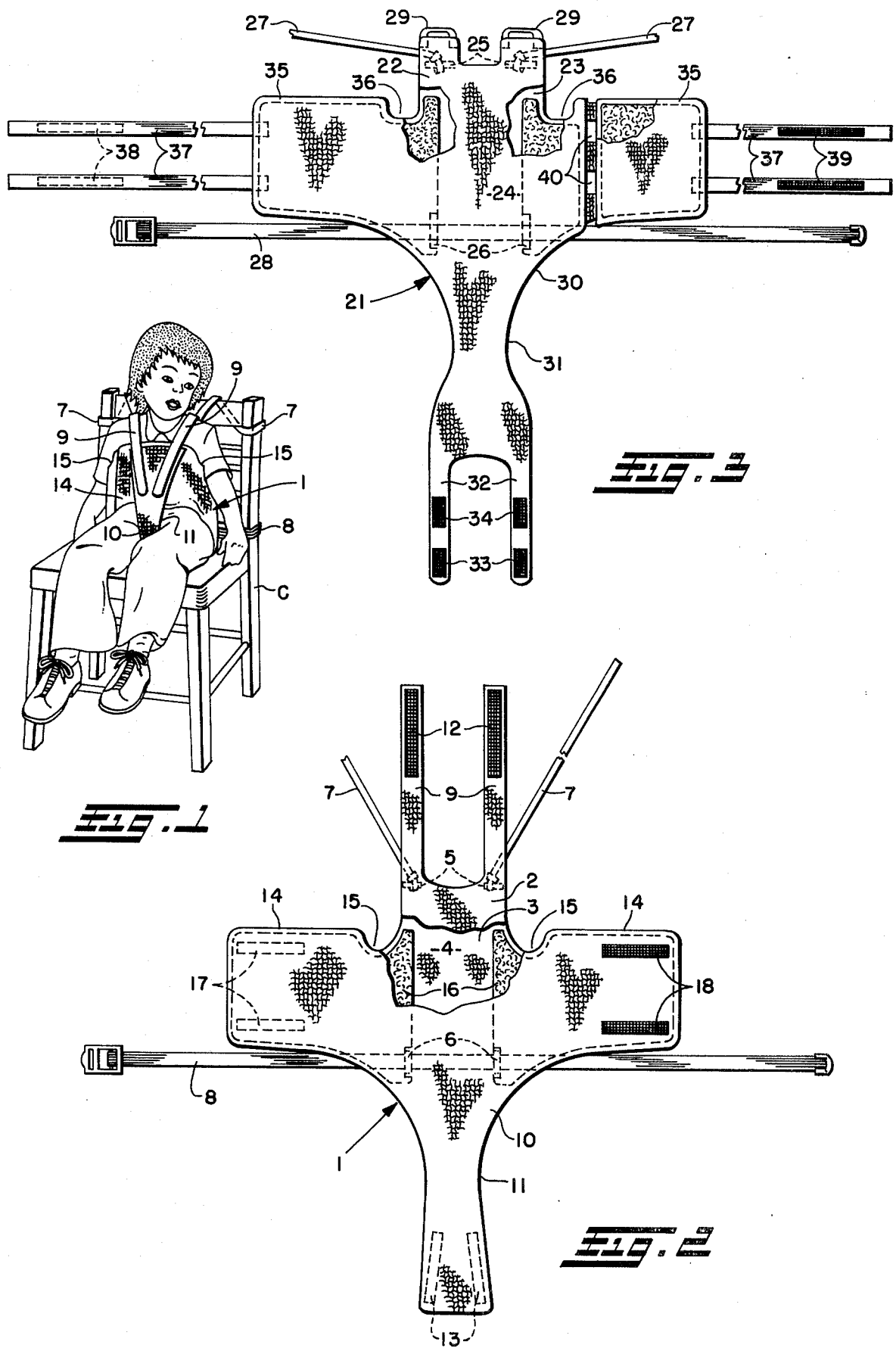

U.S. Patent  Sept. 27, 1977  Sheet 2 of 3  4,050,737
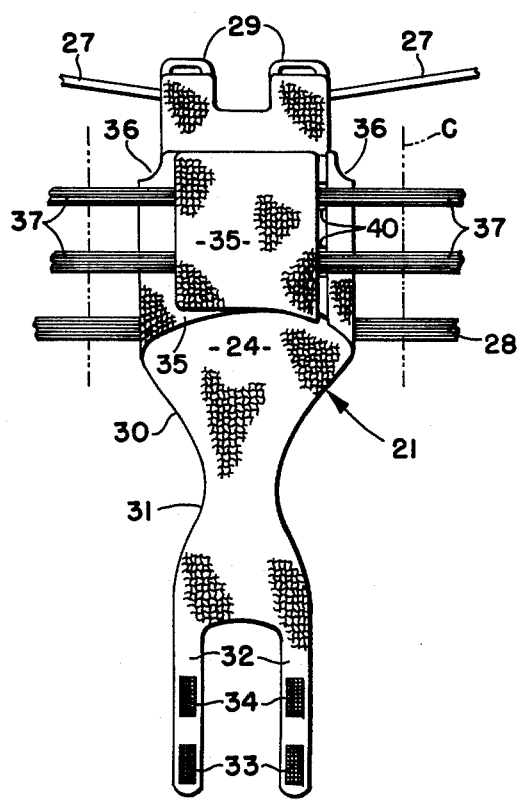
Fig. 4
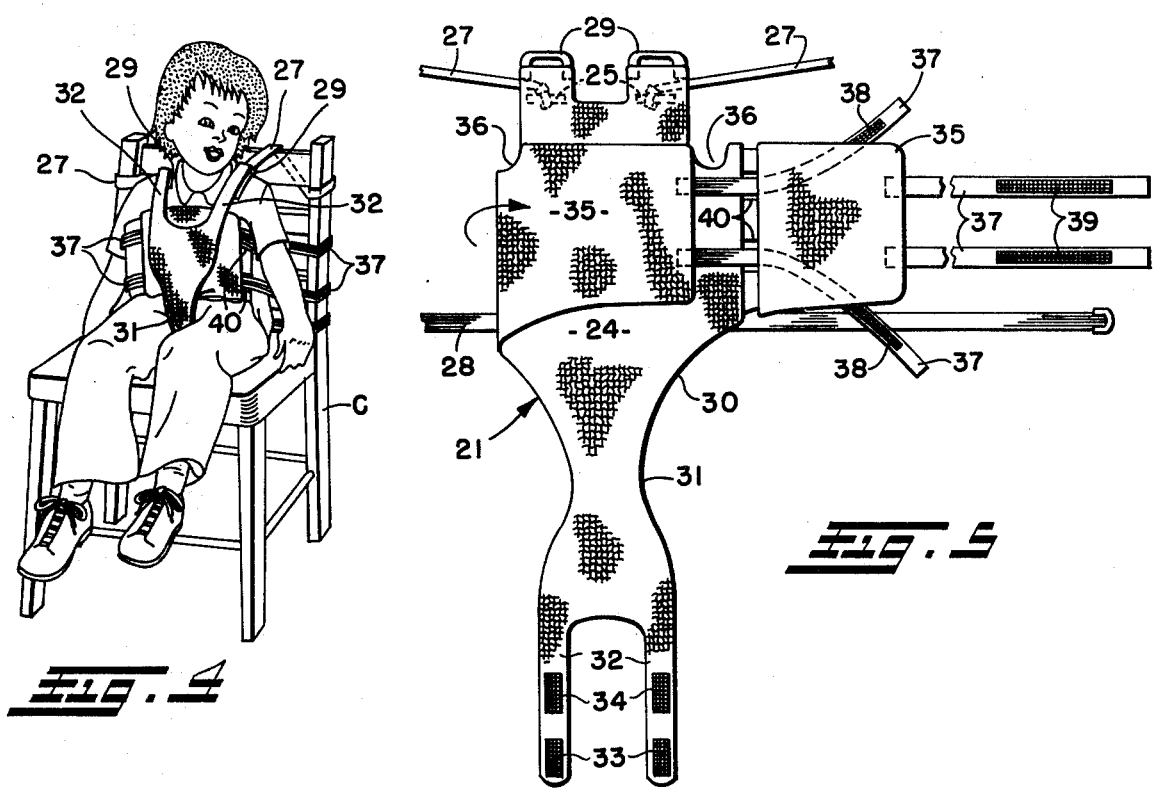
Fig. 5
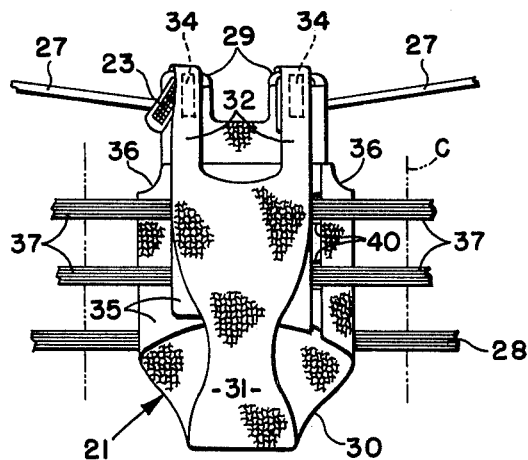
Fig. 7
Fig. 6

SUPPORT HARNESS

BACKGROUND OF THE INVENTION

One known form of support device intended for supporting a physically handicapped child in normal sitting position comprises a padded vest-like garment which embraces the child's trunk and which has mounted in the upper middle portion of the back and in the corresponding portion of the backrest of a chair mating male and female coupling parts to releasably hold that portion of the device against the backrest. However, aside from the expense and inconvenience of providing and mounting such mating coupling parts in the garment and in the backrest of the chair for access for coupling and uncoupling movement, such construction does not properly support the handicapped child in normal erect sitting position because the hips can slide sidewise and forwardly with respect to the upper middle portion of the back of the garment. Furthermore, such support device can only be used with certain chairs wherein the backrest coupling part may be mounted for access for coupling and uncoupling to and from the mating garment coupling part.

As evident, such known form of safety or support harness is not suitable for supporting a child with cerebral palsy or other neurological disease in normal sitting position.

SUMMARY OF THE INVENTION

A support harness for firmly but comfortably supporting a child with cerebral palsy or other neurologic disease in a normal sitting position in any chair or seat while the child's arms, legs, and head are completely free of any restraint. For a child subject to seizures, the support harness is provided with quick release fastening means for removing the child from the harness and the chair to which the harness is tied and strapped. On the other hand, for a hyperactive child the support harness has the quick release fastening means positioned so as not to be accessible for inadvertent release by the child.

Yet another object of this invention is to provide a support harness of the character indicated which has a flat, rigid back portion which extends the usefulness of the support harness in conjunction with a wide variety of sizes and types of chairs to support the handicapped child in normal erect sitting position with both firmness and comfort.

Other objects and advantages will appear from the ensuing description.

BRIEF DESCRIPTION OF THE DRAWING

FIG. 1 is a perspective view showing one form of support harness constituting the present invention tied to the back of a chair to support a child in normal sitting position;

FIG. 2 is a plan view of the support harness shown in FIG. 1 opened to flat form;

FIG. 3 is similar to FIG. 2 except illustrating another form of support harness;

FIG. 4 is a perspective view illustrating the harness of FIG. 3 in use in supporting a child in normal sitting position;

FIGS. 5, 6 and 7 illustrate successive steps in placing the FIG. 4 harness in child-supporting position;

DETAILED DESCRIPTION OF THE PREFERRED EMBODIMENTS

Figure 8:
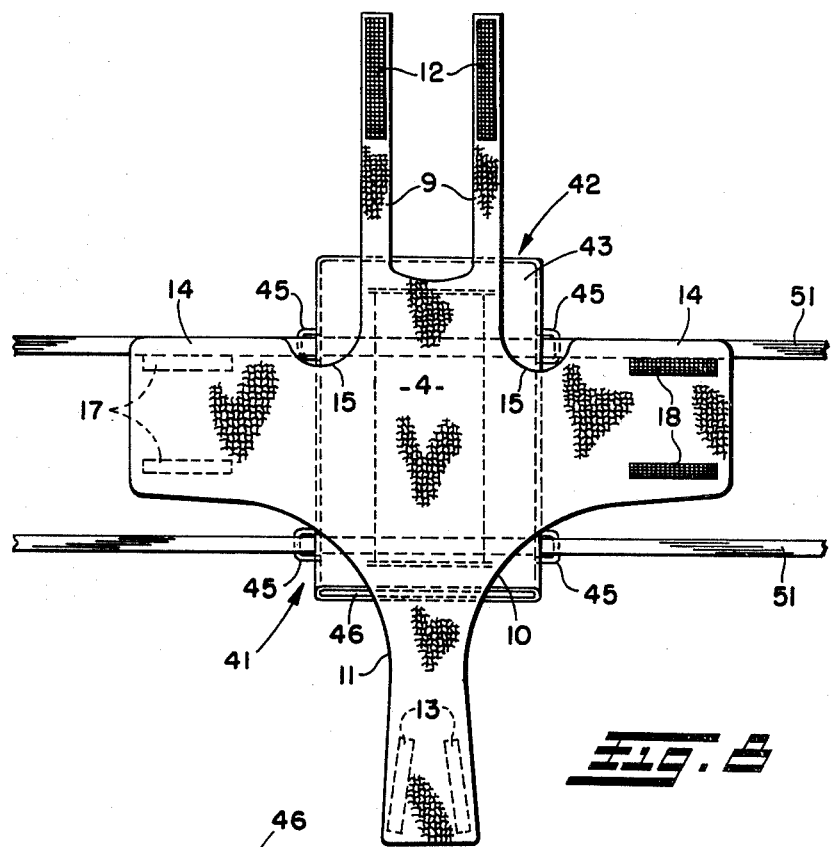
FIG. 8 is a plan view of a support harness similar to that of FIG. 2 (or FIG. 3) including a pillowcase-like back portion having therein a flat rigid back supporting member.

The support harness 1 shown in FIGS. 1 and 2 comprises two layers 2 and 3 of fabric, preferably brushed denim which combines firmness and softness, defining a generally rectangular back portion 4 having loops 5 and 6 stitched thereto at shoulder level and hip level for straps 7 and 8, the straps being removable as for laundering of the harness. Extending upwardly from the back portion 4 are shoulder straps 9 and extending downwardly from the back portion 4 is a longitudinal flap 10 which is of progressively decreasing width to define a crotch portion 11. The end portions of the shoulder straps 9 and the end portion of the longitudinal flap 10 have on opposite sides thereof cooperating adjustable quick release fastening means 12 and 13 such as Velcro strips.

Extending laterally from the back portion 4 are wings or flaps 14 which are cut out at 15 to fit under the child's armpits, the lower edges of the flaps 14 being smoothly curved and joined to the longitudinal flap 10. The flaps 14 have padding material 16, such as ¼ inch foam rubber therein, which preferably starts where the child's back curves away from the back of the chair C. The padding 16 imparts firmness to the flaps 14 without sacrificing comfort. The opposite sides of said flaps 14 have stitched thereto cooperating quick release fastening means 17 and 18 such as Velcro strips.

In the use of FIG. 2 support harness 1 it may first be secured to the chair C by wrapping the straps 7 around the upper portion of the back of the chair as shown in FIG. 1 and tying the straps 7 together behind the backrest. The strap 8 is positioned around the lower portion of the back of the chair C and buckled in place therebehind. With the shoulder straps 12 draped over the top of the chair back and with the flap 10 extending forwardly of the back of the chair, a child may be placed in sitting position and first the left flap 14 as viewed in FIG. 1 will be wrapped snugly around over one side and across the chest and abdomen of the child and then the right flap 14 as viewed in FIG. 1 will be wrapped snugly around the other side into full overlapping relation with the left flap 14 whereat the strips 17 and 18 are interengaged to hold the flaps 14 together. The crotch portion 11 is then pulled up between the child's legs and the adjacent end portion is placed against the overlapping flaps 14 for adjustably fastening the shoulder straps 9 by the interengaging the fastening strips 12 and 13.

As evident, the buckled strap 8 at the hip position and the crotch portion 11 holds the lower back of the child against the back of the chair C and prevents the child's hips from sliding forward. The tie straps 7 attached at shoulder level hold the upper end of the back portion 4 against the back of the chair C and this, in conjunction with the overlapping flaps 14, 10 and straps 9 hold the child's shoulders against the back of the chair C. The child's chest and abdomen are firmly but comfortably supported by the double layer of the padded flaps 14 and also by the overlying straps 9 and flap 10. Also, the padded areas of the flaps 14 at the sides of the child's torso assist in maintaining the child in normal sitting position. The harness 1 herein, in effect, creates an outer shell to replace or supplement the child's lack of normal muscular or neurological control through the trunk area and the child is held in normal sitting position against both forward movement and sidewise angular movement. The child is thus held comfortably and firmly in the normal sitting position and is encouraged to develop whatever potential he or she has for neck and head control. The child's arms, legs, and head are completely free of any restraint.

For a child who is subject to seizures, the harness 1 may be quickly opened by pulling the shoulder straps 9 and the top flap 14 to disengage the strips 12-13 and 17-18.

Referring now to the support harness 21 shown in FIGS. 3-7, it, as best shown in FIG. 3, comprises two layers 22 and 23 of fabric e.g. brushed denim defining a generally rectangular back portion 24 having loops 25 and 26 at shoulder level and hip level for the straps 27 and 28 as in the case of the FIG. 2 embodiment. However, in FIG. 3 the upper end of the back portion 24 has extensions with shoulder strap loops 29 and the lower end has a longitudinal flap 30 which is of progressively narrowing width to a crotch portion 31. The end portion of flap 30 terminates in shoulder straps 32 each of which carries on its front side as viewed in FIGS. 3, 5 and 6 cooperating quick release strips 33 and 34 which are adapted to be passed through the loops 29 and fastened as shown in FIGS. 4 and 7.

In FIG. 3, the padded and laterally extending wings or flaps 35 have armpit cutouts 36 similar to those in FIG. 2 and flexible straps 37 are stitched in the ends of the flaps 35, said straps 37 having quick release fastening strips 38 and 39 stitched on opposite sides thereof. The righthand flap 35 has two slots 40 therethrough to receive the straps 37 of the lefthand flap 35 when it is folded as in FIG. 5. When the righthand flap 35 is folded as in FIG. 6, the straps 37 of both flaps 35 pass over the sides of the backrest of the chair C and are fastened together by strips 38-39 behind the back of the chair C.

With the flaps 35 and back portion 24 disposed around the child's trunk from the armpits to the hips and from the chest to the abdomen, the longitudinal flap 30 may be pulled up through the child's crotch and upwardly over the abdomen and chest as shown in FIG. 4 (also FIG. 7) whereupon the shoulder straps 32 may be inserted through the loops 29 and fastened as shown in FIG. 7 by pressing the cooperating quick release fastening strips 33-34 together.

As shown in FIG. 4, the child is firmly and comfortably supported in normal sitting position in the chair C, with complete freedom of the arms, legs, and head. However, in the case of a hyperactive child there is no way that the child can inadvertently free himself from the harness 21 because the quick release fastening means 38-39 are behind the back of the chair C. Moreover, it is rather difficult for the child to unfasten the shoulder straps 32 because it requires pulling apart of fastening strips 33-34.

Although the support harnesses 1 and 21 herein shown are used in connection with a conventional chair C with an exposed frame, it is to be understood that these harnesses may be secured to most any chair or seat used in the home, school, hospital, etc. or such as those provided in a car seat, stroller, or wheelchair.

Figure 9:
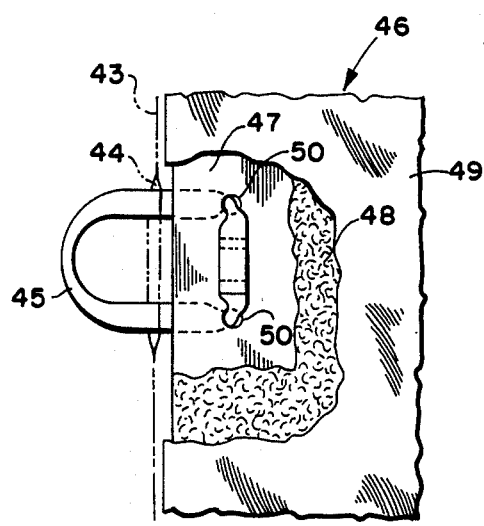
FIG. 9 is a fragmentary enlarged view of a portion of the rigid back supporting member of the FIG. 8 support harness.
Figure 10:
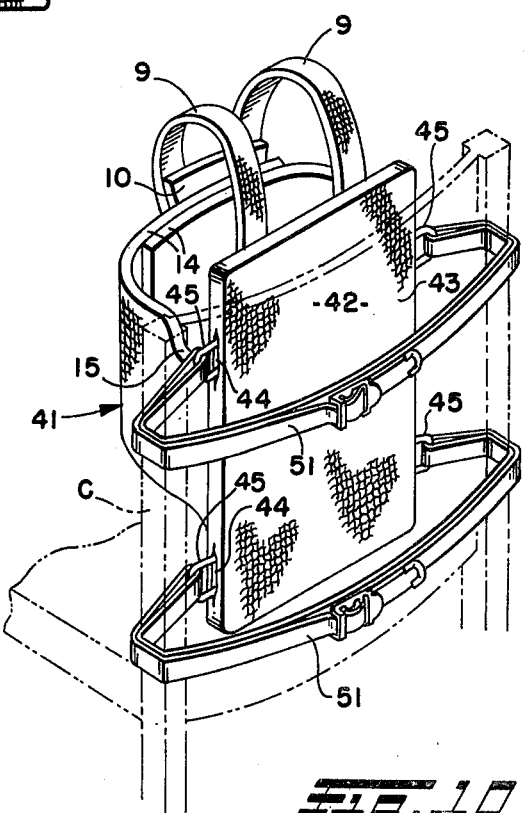
FIG. 10 is a perspective view showing how the support harness of FIG. 8 is secured to the backrest of a chair to provide a flat backrest for the physically handicapped child.

Referring now to FIGS. 8, 9 and 10, the support harness 4 may be the same as illustrated in FIGS. 1 and 2 except for the omission of the loops and straps 5, 6 and 7, 8 and the addition of a rigid flat back support 42. In this case, the back portion 4 has stitched thereto as shown the front side of a pillowcase-like fabric member 43 (brushed denim, for example) which is open at the bottom and which has openings 44 on opposite sides at shoulder and hip levels through which loops 45 of a flat rigid back support member 46 project when the latter is inserted upwardly through the open bottom of the member 43. As best shown in FIG. 9, the back support member 46 comprises a rectangular piece of hardboard or particle board 47 of, for example, 3/16 inch thickness having a layer of foam rubber 48 or the like on its front side and the board 47-48 is encased in flexible plastic 49. Each loop 45 may comprise a strip of flexible plastic material inserted through drilled holes 50 in the board 47 with the ends stitched together as shown.

As shown in FIG. 10, the harness 41 is securely mounted to the backrest of a chair C by belts 51 buckled behind the backrest at the shoulder and hip levels, the belts 51 extending through the loops 45 and over the sides of the backrest. In connection with a rounded back chair as shown in FIG. 10, or a ladder back or vertical spindle chair the harness 41 provides a comfortable flat back-support 42. In the case of a large size deep chair, one or more foam rubber pillows or the like may be interposed between the back support 42 and the backrest of the chair so that the child's legs may comfortably hang from the front edge of the chair while yet the child's trunk is comfortably and firmly supported in normal erect sitting position with freedom of arm, head and leg movement as described in connection with FIGS. 1 through 7.

Although in FIGS. 8, 9 and 10 the support harness 41 is like that shown in FIGS. 1 and 2, it is to be understood that the pillowcase-like member 43 for receiving the flat rigid back support member 46 may be stitched to the back portion 24 of the harness 21 of FIGS. 3 to 7 and, of course, in place of the straps 27 and belt 28, the belts 51 will be used as shown in FIG. 10 to provide the necessary supports at shoulder and hip levels.

In summary therefore, the present support harness provides firm and comfortable support for a child who, due to brain damage or disease, lacks trunk or head control or lacks normal balance control to such an extent that he or she is unable to achieve or maintain a sitting position. The harness herein provides both firm and comfortable support to support the child in normal sitting position with complete freedom of the arms, legs, and head. Furthermore, the principles of the present invention may be embodied in an adult-size harness for supporting an adult invalid in normal sitting position.

As evident, the releasable fasteners enable adjustment to different size children by varying the overlap of the fastener strips when pressed together. The harnesses 1, 21, and 41 herein may be hand or machine laundered, preferably with the straps 7 and 8 (FIG. 2) or straps 27 and 28 (FIG. 3) or belts 51 and back support member 46 (FIG. 8) removed, in cool or lukewarm water so as not to damage the padding in the flaps 14 or 35 and may be line or tumble dried.

The embodiments of the invention in which an exclusive property or privilege is claimed are defined as follows:

1. A support harness for firmly and comfortably supporting a child with cerebral palsy and the like against the back of a chair in normal sitting position comprising a back portion having means at shoulder and hip levels for detachably securing said back portion to the back of a chair; padded lateral flaps at opposite sides of said back portion of length and width for wrapping around a child's torso over the sides thereof and overlapping each other over the entire chest and abdomen, said lateral flaps and padding therein naving cutouts to fit under the child's armpits for freedom of arm movement; releasable fastener means for securing said flaps in such overlapping relation; a longitudinal flap from the lower end of said back portion of progressively narrowing width to extend forwardly from the back of the chair under the child's hips and to extend upwardly through the child's crotch to overlie said overlapped lateral flaps substantially to the upper edges thereof; and shoulder straps including releasable fastener means to interconnect the upper end of said back portion to the end portion of said longitudinal flap, said lateral flaps and said longitudinal flap when wrapped around a child's trunk as aforesaid forming leg openings at the upper portions of the thighs for freedom of leg movement while the child is retained in normal erect sitting position; the padding in said lateral flaps beginning inwardly of said cutouts in the region of the back portion where the child's back curves away from the back of the chair thus to stiffen, without sacrifice of comfort, the portions of the harness which embrace the sides of the child's trunk.

2. The support harness of claim 1 wherein said shoulder straps constitute longitudinal extensions from the upper end of said back portion, the end portions of said shoulder straps and the end portion of said longitudinal flap having said releasable fastener means thereon which comprise flexible strips on said shoulder straps and longitudinal flap which when pressed together stick to each other and which are released by pulling said shoulder straps away from said longitudinal flap.

3. The support harness of claim 1 wherein said longitudinal flap has longitudinal shoulder straps releasably secured to the upper end of said back portion; each shoulder strap having said cooperating releasable fastener means and the upper end of said back portion has loops through which the end portions of said shoulder straps are folded under and secured to said loops by said fastener means.

4. The support harness of claim 1 wherein each lateral flap has a flexible strap secured thereto and extending beyond its end; and wherein one lateral flap outwardly adjacent the armpit cutout has a slot therethrough to receive the strap of the other flap when wrapped over the chest and abdomen with said strap adapted to extend over the adjacent side of the backrest of a chair, the strap of said one flap adapted to extend over the other side of the backrest, said straps having overlapping portions behind said backrest containing said fastener means to retain said flaps in overlapping relation over the chest and abdomen.

5. The support harness of claim 1 wherein said back portion has secured thereto a flat rigid back support having loops on opposite sides for belts constituting said means at shoulder and hip levels for detachably securing said back portion to the back of a chair; said back support being of width extending to the armpit cutouts but being secured to said back portion within said cutouts to enable wrapping of said lateral flaps over the portions of the child's back curving away from said back support.

6. A support harness for firmly and comfortably supporting a child with cerebral palsy and the like against the back of a chair in normal sitting position comprising a back portion having means at shoulder and hip levels for detachably securing said back portion to the back of a chair; padded lateral flaps at opposite sides of said back portion of length and width for wrapping around a child's torso over the sides thereof and overlapping each other over the chest and abdomen, said flaps having cutouts to fit under the child's armpits for freedom of arm movement; releasable fastener means for securing said flaps in such overlapping relation; a longitudinal flap from the lower end of said back portion of progressively narrowing width to extend forwardly from the back of the chair under the child's hips and to extend upwardly through the child's crotch to overlie said overlapped lateral flaps; and shoulder straps including releasable fastener means to interconnect the upper end of said back portion to the end portion of said longitudinal flap, said lateral flaps and said longitudinal flap when wrapped around a child's trunk as aforesaid forming leg openings at the upper portions of the thighs for freedom of leg movement while the child is retained in normal erect sitting position; said back portion having secured thereto a flat rigid back support having loops on opposite sides for belts constituting said means at shoulder and hip levels for detachably securing said back portion to the back of a chair; said back support comprising a pillowcase-like member open at one end for insertion of a board-like member having said loops extending through openings in opposite sides of said pillowcase-like member.

7. The support harness of claim 6 wherein said board-like member has padding material on its front side and is encased in flexible plastic sheet material.

8. The support harness of claim 6 wherein said pillowcase-like and board-like members are of width extending to the armpit cutouts with said pillowcase-like member being secured to said back portion within said cutouts to enable wrapping of said lateral flaps over the portions of the child's back curving away from said back support.

* * * * *